(12) United States Patent
Wilkening et al.

(10) Patent No.: US 6,171,245 B1
(45) Date of Patent: Jan. 9, 2001

(54) METHOD OF IMAGING SCATTERERS BASED ON ACOUSTICALLY STIMULATED CHANGES OF THEIR ACOUSTIC PROPERTIES

(75) Inventors: Wilko Wilkening, Bochum (DE); John Lazenby, Fall City, WA (US)

(73) Assignee: Siemens Medical Systems, Inc., Iselin, NJ (US)

( * ) Notice: Under 35 U.S.C. 154(b), the term of this patent shall be extended for 0 days.

(21) Appl. No.: 09/267,892

(22) Filed: Mar. 11, 1999

Related U.S. Application Data

(60) Provisional application No. 60/077,807, filed on Mar. 12, 1998.

(51) Int. Cl.$^7$ ........................................................ A61B 8/00
(52) U.S. Cl. ............................................................. 600/458
(58) Field of Search ........................... 600/437, 454–456, 600/458

(56) References Cited

U.S. PATENT DOCUMENTS

| | | | |
|---|---|---|---|
| 5,255,683 | * 10/1993 | Monaghan | 600/458 |
| 5,456,257 | * 10/1995 | Johnson et al. | 600/458 |
| 5,526,816 | * 6/1996 | Arditi | 600/458 |
| 5,577,505 | * 11/1996 | Brock-Fisher et al. | 600/458 |
| 5,601,086 | * 2/1997 | Prettow, III et al. | 600/458 |
| 5,716,597 | * 2/1998 | Lohrmann et al. | 600/458 |
| 5,737,707 | * 4/1998 | Widder et al. | 600/458 |
| 5,961,464 | * 10/1999 | Poland | 600/458 |
| 5,980,460 | * 11/1999 | Østensen et al. | 600/458 |

* cited by examiner

*Primary Examiner*—Francis J. Jaworski

(57) ABSTRACT

A method of imaging blood with the use of contrast agents. A sequence or ensemble of imaging pulses is transmitted into a patient. Echo signals received in response to each of the imaging pulses are received and analyzed to determine if the echoes are produced by tissue or by the contrast agent. Echoes produced by the contrast agent are detected by an echo signal that changes in amplitude or a centroid frequency that changes with each imaging pulse. Once the location of the contrast agent has been determined, an image is created whereby the contrast agent is highlighted for view by a physician or sonographer.

9 Claims, 2 Drawing Sheets

METHOD OF IMAGING SCATTERERS BASED ON ACOUSTICALLY STIMULATED CHANGES OF THEIR ACOUSTIC PROPERTIES

RELATED APPLICATIONS

This application claims the benefit of U.S. Provisional Application No. 60/077,807, filed Mar. 12, 1998.

FIELD OF THE INVENTION

The present invention relates to ultrasound imaging in general, and in particular to methods of imaging slowly moving blood flow using contrast agents.

BACKGROUND OF THE INVENTION

Many diseases in the human body can be detected by analyzing the flow of blood through tissue. For example, tumors are often characterized by tissue having little or no blood flowing into them.

One commonly used technique to analyze the blood flow is ultrasound imaging. While this technique works well for producing images of fast moving blood flow, such as that found in arteries or major veins, it is difficult to produce images of blood moving in capillaries or small vessels because the echo signals produced by the individual blood cells are small in relation to the echoes produced by surrounding tissue and because the blood is moving too slow to accurately image using Doppler techniques.

To enhance the ability of slowly moving or stationary blood to produce strong echo signals, it is often advantageous to introduce a contrast agent into the patient. Typically, contrast agents are liquids containing small gas bubbles that are surrounded by a coating or shell. These bubbles produce stronger echo signals when subjected to ultrasound pulses than the blood cells do. While the use of a contrast agent increases the ability of an ultrasound machine to produce images of blood, it is still difficult to resolve blood in capillaries due to the small amount of contrast agent present at a particular location in the body. In addition, the current techniques for detecting the contrast agent are sensitive to motion artifacts caused by movement of the body or of the ultrasound probe.

Given the above shortcomings in the art, there is a need for a new ultrasound imaging mode that can accurately capture images of slowly moving blood flow or stationary blood.

SUMMARY OF THE INVENTION

The present invention is a technique for producing ultrasound images of slowly moving blood flow or stationary blood by isolating echo signals produced by a contrast agent from those produced by surrounding tissue. To produce an ultrasound image, a series or ensemble of ultrasound pulses are directed into the body along a single beam line. Echo signals created in response to each of the pulses are received and analyzed to separate those echo signals produced by the contrast agent from those produced by surrounding tissue.

To separate the echo signals, the echo signals are preferably analyzed for characteristic changes in their amplitude or centroid frequency. An image is then created wherein that portion of the body that produces the echo signals exhibiting the expected changes are highlighted while those areas of the body that produce substantially constant echo signals are not.

The present invention allows blood flow to be imaged in a manner that is less sensitive to tissue or probe movement.

BRIEF DESCRIPTION OF THE INVENTION

DETAILED DESCRIPTION OF THE PREFERRED EMBODIMENT

As indicated above, the present invention is a method for isolating those ultrasound echo signals produced by a contrast agent from those produced by surrounding tissue. By isolating the echo signals created from a contrast agent, an image is created whereby slowly moving blood flow or stationary blood can be indicated.

Figure 1:
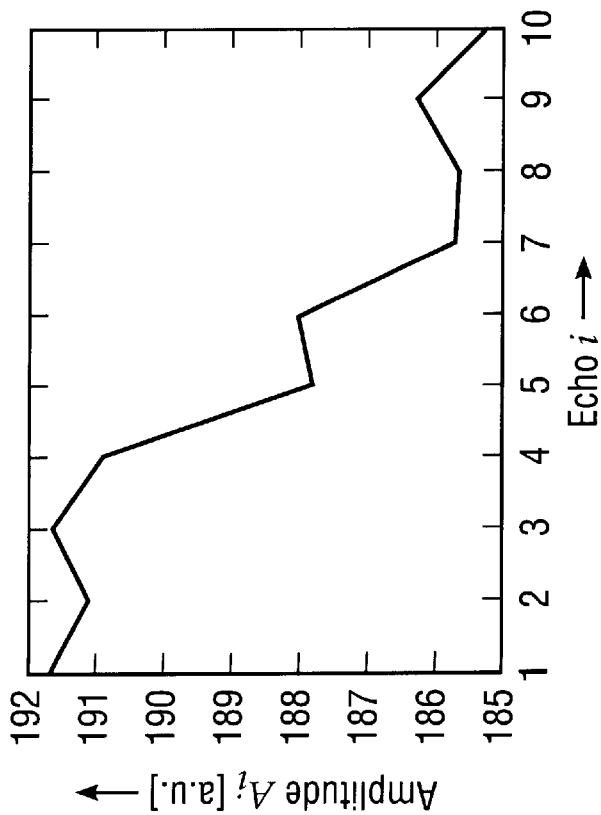
FIG. 1 is a graph of an expected change in the amplitude of echo signals produced by a contrast agent when subjected to multiple ultrasound pulses.

When a contrast agent is subject to ultrasonic imaging pulses, the microbubbles oscillate in a non-linear manner which is determined by the resonant frequency of the individual bubbles. The resonant frequency depends, among other things, on the diameter of the bubble, the gas filling as well as the shell material used and its thickness. FIG. 1 illustrates one change in echo amplitude as a sample of ultrasound contrast agent is subjected to a series of ultrasound pulses. In the example used, the contrast agent is Levovist® produced by Schering AG. As can be seen, the amplitude of the echo signals decreases in a generally linear manner due to the destruction of the individual gas bubbles by the pulses and the dissolving of the gas in the surrounding blood.

Figure 2:
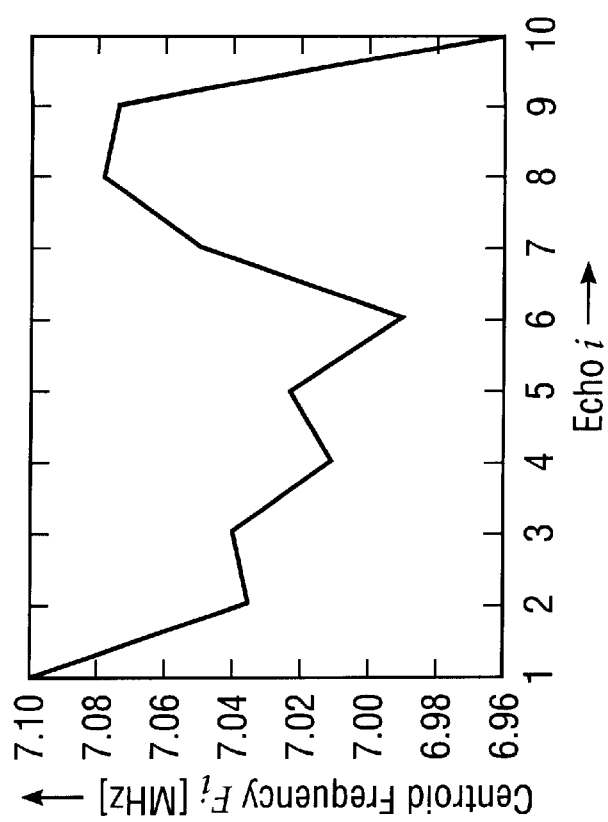
FIG. 2 is a graph of an expected change in the centroid frequency of an echo signal produced by a contrast agent when subjected to multiple ultrasound pulses.

In addition to a decrease in echo amplitude, it has been determined that the centroid frequency of a sample of contrast agent will change when subjected to the number of ultrasound pulses. As shown in FIG. 2, the centroid frequency has been found to decrease from a maximum in response to a first number of ultrasound pulses followed by an increase in the centroid frequency as additional pulses are fired.

Once it is known how the echo characteristics, such as the amplitude or centroid frequency of a contrast agent behave in response to a sequence of ultrasound pulses, the echo signals received from a body including a contrast agent can be analyzed in order to separate those echo signals produced by contrast agent from those produced by surrounding tissue. It will be appreciated that the data shown in FIGS. 1 and 2 will depend upon the type of contrast agent used, its concentration and other factors. Therefore, data regarding an expected behavior of the particular contrast agent will have to be obtained in order to accurately distinguish echo signals from the contrast agent versus the surrounding tissue.

Figure 3:
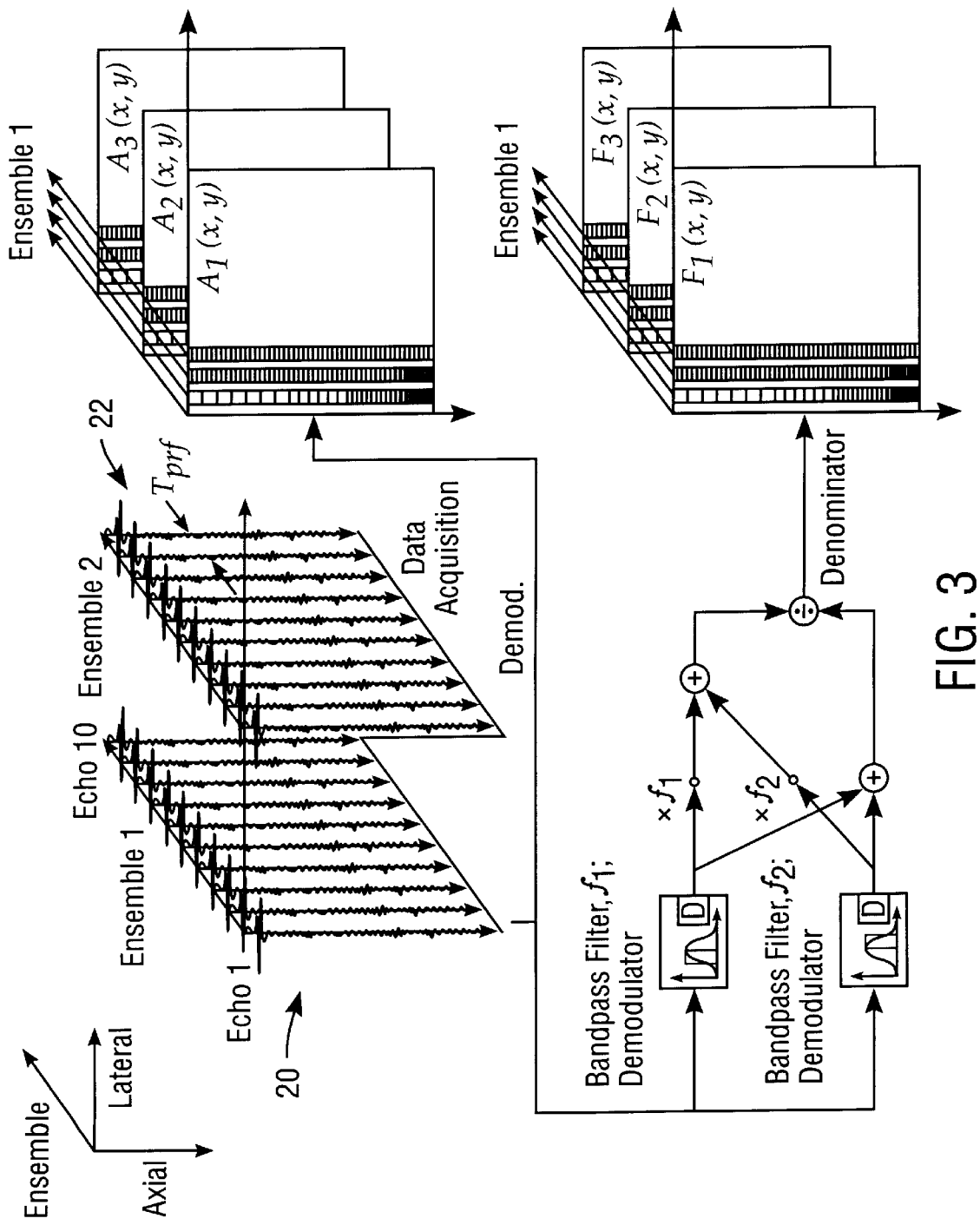
FIG. 3 illustrates a technique for separating echo signals received from a contrast agent from those echo signals produced by surrounding tissue according to the method of the present invention.

FIG. 3 illustrates how the present invention operates to isolate those echo signals produced by a contrast agent in slowly moving or stationary blood from those echo signals produced by surrounding tissue. To produce an ultrasound image in which blood flow, i.e., blood in capillaries or other tissue can be more easily viewed, an ultrasound system of the conventional type including a transducer, beamformer, image processor and video monitor is programmed to transmit a sequence or ensemble of pulses 20 along a single beam line. In the example shown, ten pulses are transmitted and the echo signals created in response to the pulses are received and stored in a digital memory for analysis. After the analysis, the beam line is then changed and a second series or ensemble of pulses 22 is transmitted, and the echo signals created in response to these pulses are stored and analyzed. This process continues until echo signals have been transmitted on a sufficient number of beam lines to create an image of the tissue under examination.

As indicated above, the echo signals produced by a contrast agent within the body vary in both amplitude and frequency in response to each of the sequential ultrasound pulses applied. Conversely, the echo signals produced by tissue remain substantially the same in response to each ultrasound pulse. Therefore, by analyzing the echo signals received from a particular depth in the tissue in response to each of the pulses applied, the echo signals produced by the tissue can be separated from those produced by the contrast agent. Once it is determined if the source of the echo at any particular depth is the contrast agent or the surrounding tissue, an image is created whereby the slowly moving or stationary blood flow is highlighted or otherwise indicated.

One characteristic of the echo signals produced by a contrast agent in response to a series of ultrasound pulses that differentiates them from those signals produced by tissue is an amplitude or envelope which changes with each ultrasound pulse. Several measures of the changing amplitude can be used to determine whether the echo signals are being produced by stationary tissue or by a contrast agent. The first measure is the standard deviation of the echo amplitude, which can be defined $$\sigma_A(x, y) = \sqrt{\frac{1}{N-1} \sum_{i=1}^{N} (A_i(x, y) - \mu_A(x, y))^2}, \quad (1)$$

$$\mu_A(x, y) = \frac{1}{N} \sum_{i=1}^{N} A_1(x, y)$$

If the standard deviation of the echo amplitudes matches that which is expected to be produced by a contrast agent, then the source of the echoes at that particular depth is assumed to be contrast agent and is shown in a brightness or color which varies according to the standard deviation and thus will highlight the blood flow or tissue containing the contrast agent.

An alternative method of detecting those echo signals produced by a contrast agent is to calculate the maximum amplitude swing of the amplitude which can be defined as:

$$\Delta(x,y) = \max(A(x,y)) - \min(A(x,y)) \quad (2)$$

If the maximum echo amplitude detected exceeds the minimum echo amplitude detected by more than some preset or precalculated value, then it is assumed that the source of the echo signals is the contrast agent and that portion of the ultrasound image can be appropriately indicated. Those echo signals produced by the surrounding tissue that does not contain a contrast agent will have a substantially constant magnitude and therefore the maximum amplitude swing will be less than the predetermined value.

A third, more robust parameter is obtained by correlating the received echo amplitudes at each given depth with the expected amplitude change for a contrast agent according to the equation:

$$\rho_A(x, y) = \frac{\sum_{i=1}^{N} [A_{i,ref} - \mu_{A,ref}] [A_i(x, y) - \mu_A(x, y)]}{\sqrt{\sum_{i=1}^{N} (A_{i,ref} - \mu_{A,ref})^2 \sum_{i=1}^{N} (A_i(x, y) - \mu_A(x, y))^2}}, \quad (3)$$

$$A_{ref} = [A_{1,ref}, A_{2,ref}, \ldots A_{N,ref}],$$

$$\mu_{A,ref} = \frac{1}{N} \sum_{i=1}^{N} A_{i,ref}$$

where $A_{ref}$ is a reference or expected amplitude curve which is typical for a sonified contrast agent such as the data shown in FIG. 1. If the echo signals received correlate closely with the expected results, it is assumed that the source of the echo at that depth in the tissue is a contrast agent and can be shown as such in the ultrasound image.

A fourth parameter, $p_A(x,y)$, is less sensitive to noise than those previously described. The basic idea is that processes which change the acoustic properties of insonified bubbles should only take place once throughout the ensemble. There should not be any repetitions. Since $A_t(x,y)$ represents the course in time of a parameter that characterizes the time-variance, where i denotes a position in time, the discrete Fourier transform (or spectrum) of $A_t(x,y)$ allows the characterization of the time-variance based on spectral parameters. $A_t(x,y)$ is a real signal, therefore, the spectrum is symmetrical. $S_{A+}(f)$ denotes the right half of the absolute value of the spectrum (or alternatively the power spectrum) excluding the DC($f=0$). Note that $S_{A+}(f)$ is the spectrum of the amplitude or envelope detected echo signals, rather than the spectrum of the echo signals themselves. If $A_t(x,y)$ results from stationary scatterers or stationary scatterers and white noise, then $S_{A+}(f)$ should be either zero or approximately constant for all considered frequencies. If $A_t(x,y)$ results from insonified bubbles, there should be higher amplitudes at low frequencies and lower amplitudes at high frequencies, indicating that a process starts at some point and continues throughout the ensemble. It is not important when the process actually starts or whether it causes the parameter, i.e., the amplitude, to increase or to decrease. We compare $S_{A+}(f)$ to a decaying exponential $c^{-i}$ by means of a correlation coefficient. Assuming that $S_{A+}(f)$ is given at M frequencies, the correlation coefficient can be written as:

$$\rho_{A,S} = \frac{\sum_{i=1}^{M} [S_{A+}(f_i, x, y) - \mu_s(x, y)] \cdot [c^{-i} - \mu_c]}{\sqrt{\sum_{i=1}^{M} (S_{A+}(f_i, x, y) - \mu_s(x, y))^2 \sum_{i=1}^{M} (c^{-i} - \mu_c)^2}}, \quad (4)$$

c=const, where $$\mu_s(x, y) = \frac{1}{N} \sum_{i=1}^{M} S_{A+}(f_i, x, y), \quad \mu_c = \frac{1}{N} \sum_{i=1}^{M} c^{-i} = \frac{1 - c^{-M}}{N(c - 1)} \quad (5)$$

The closer the correlation coefficient is to 1, the better $S_{A+}(f)$ matches the decaying exponential. Therefore, we define threshold t and let:

$$p_A = \begin{cases} 0 & \rho_{A,S} < t \\ \rho_{A,S} & \rho_{A,S} \geq t, \end{cases} \quad 0 \leq t \leq 1, \text{ typ.: } 0.3 \leq t \leq 0.9 \qquad (6)$$

The constant c can be chosen experimentally. Setting c≈2.7183 (Euler's number) gave good results.

Displaying the product $\sigma_A \cdot p_A$ in a logarithmic scale combines the advantages of both parameters, where $\sigma_A$ provides information on the concentration of the contrast agent and $p_A$ reduces the sensitivity to noise artifacts.

An additional parameter which can be used to separate those echo signals produced by a contrast agent from those produced by tissue is a change in their centroid frequency. The spectrum at any given depth in the tissue can be estimated by calculating Fourier transforms of the echo signals within a number of short overlapping windows. An alternative approach to calculating the centroid frequency is to divide the received spectrum into two or more frequency bands and to calculate the amplitude of the echo signals in those frequency bands. The amplitudes which are near the center frequency of the bandpass filters represent the local spectrum at discrete frequencies. The centroid frequency is given by:

$$F_i(x, y) = \frac{\int_{f_{min}}^{f_{max}} f \cdot S_i(f, x, y) df}{\int_{f_{min}}^{f_{max}} S_i(f, x, y) df} \qquad (7)$$

$$F(x, y) = [F_1(x, y), F_2(x, y), \ldots F_N(x, y)]$$

where N denotes the ensemble size or number of ultrasound pulses fired on the same beam line, and $f_{min}$, $f_{max}$ are the cut-off frequencies of the considered bandwidth and S is the signal power at a particular position and i denotes a particular firing in an ensemble. A typical curve representing the change in the centroid frequency for the contrast agent Levovist® within a sponge is shown in FIG. 2. Better performance may be obtained by calculating an approximation to the centroid of the spectrum. This is accomplished by dividing the spectrum into two frequency bands $f_1$ and $f_2$. The centroid (minus a constant) can then be approximated by $$F_i(x,y) = S_i(f_1,x,y) - S_i(f_2,x,y)$$

instead of performing the calculation Equation 4.

The standard deviation $\sigma_F$, and frequency swing $\Delta_F$ and the parameter $p_F$ may be calculated in a manner analogous to calculation of $\sigma_A$, $\Delta_A$ and $p_A$ by using centroid data F in place of amplitude data A. The product $\sigma_F \, p_F$ provides sensitive differentiation between contrast agent and tissue signals, just as $\sigma_A \, p_A$ does.

The signal changes that are used to discriminate contrast agents from tissue are caused by the insonification. However, in some cases the ultrasound pulses used for imaging may not be ideal for causing these changes. For example, the center frequency may be too high or the duration of the pulses may be too short. In those cases, a further aspect of this invention involves transmitting additional ultrasound pulses at other times or other frequencies than the measurement pulses. For example, a high-energy pulse can come before the measurement pulse ensemble to rupture the shell of the contrast agent bubbles. The measurement pulses can then track the decay of the bubbles. High-energy pulses may also be interleaved between the measurement pulses to ensure ongoing changes in the contrast agent. Another possibility is to combine a low frequency, long duration pulse with a higher frequency measurement pulse. The low frequency pulse may come immediately before, immediately after, or summed and simultaneous with the measurement pulse. A high pass filter on receive removes the echo resulting from the low frequency pulse and allows the formation of an image using only echoes from the measurement pulses.

By separating those signals identified as originating from a contrast agent versus those echo signals produced by tissue, it is possible to produce an image that highlights slowly moving blood flow in tissue and can allow a physician or sonographer to more readily identify potentially diseased tissue. Because the echo signals are analyzed with respect to their envelope or power spectrum instead of their phase, the method of the present invention is not as sensitive to tissue or transducer movement as other multi-pulse techniques such as power mode imaging.

We claim:

1. A method of producing ultrasound images of tissue and blood into which a contrast agent has been added, comprising:
    transmitting a sequence of three or more ultrasound pulses into a patient to induce acoustic changes in the contrast agent;
    receiving echo signals created in response to the pulses transmitted;
    analyzing each of the echo signals to identify those echo signals exhibiting acoustic changes induced by the sequence of ultrasound pulses in order to identify the location of the contrast agent and those echo signals not exhibiting induced acoustic changes to identify the location of tissue; and
    producing an image in which the sources of the echo signals that are identified to be contrast agent are indicated.

2. The method of claim 1, wherein the step of analyzing the echo signals comprises:
    analyzing the amplitude of each of the echo signals received from substantially the same depth in the tissue; and
    determining whether the amplitudes vary in response in a manner that is characteristic of tissue or contrast agent.

3. The method of claim 2, wherein the step of determining whether the amplitudes vary in a manner that is characteristic of tissue or contrast agent comprises:
    comparing the amplitude of each of the echo signals received from substantially the same depth in the tissue with data representing an expected variation in amplitude with a sequence of ultrasound pulses.

4. The method of claim 3, wherein the step of comparing the amplitudes with the data representing the expected variation in amplitude comprises:
    correlating the amplitude of each of the echo signals received from substantially the same depth in the tissue with data representing an expected variation in amplitude with a sequence of ultrasound pulses, wherein a portion of the image is identified as a contrast agent if the amplitude of the echo signals has an expected correlation to the data representing the variation in amplitude.

5. The method of claim 2, further comprising:
    transmitting ultrasound pulses having a different amplitude or frequency at the same time in order to induce acoustic changes in the contrast agent; and
    removing the echo signals induced in response to the one or more of the ultrasound pulses using a filter.

6. The method of claim 1, wherein the step of analyzing the echo signals comprises:

analyzing a centroid frequency of each of the echo signals received from substantially the same depth of tissue;

determining whether the centroid frequency varies in a manner that is characteristic of tissue or contrast agent.

7. The method of claim 1, further comprising:

transmitting one or more ultrasound pulses in the sequence of ultrasound pulses having a different amplitude or frequency in order to induce acoustic changes in the contrast agent.

8. The method of claim 1, further comprising:

transmitting one or more additional ultrasound pulses having a different amplitude or frequency between pulses having substantially the same amplitude or frequency in order to induce acoustic changes in the contrast agent; and removing the echo signals produced in response to the ultrasound pulses having a different amplitude or frequency using time gating.

9. An ultrasound system comprising:

a transducer that directs a sequence of three or more ultrasound pulses into a patient in order to stimulate acoustic changes in a contrast agent and receives echo signals created in response to each of the ultrasound pulses;

a beamformer that creates echo data from the echo signals received;

an image processor that analyzes the echo data to identify those echo signals that exhibit the acoustic changes and are indicative of the contrast agent and those echo signals produced by surrounding tissue, the image processor producing an image in which position of the contrast agent is identified; and a monitor that displays the image produced by the image processor.

* * * * *